(12) United States Patent
Nagai et al.

(10) Patent No.: US 11,619,628 B2
(45) Date of Patent: Apr. 4, 2023

(54) DEVICE AND DETERMINATION SYSTEM USING SAME

(71) Applicant: Osaka University, Osaka (JP)

(72) Inventors: Takeharu Nagai, Osaka (JP); Yoshiyuki Arai, Osaka (JP); Megumi Iwano, Osaka (JP)

(73) Assignee: Osaka University, Osaka (JP)

( * ) Notice: Subject to any disclaimer, the term of this patent is extended or adjusted under 35 U.S.C. 154(b) by 656 days.

(21) Appl. No.: 16/483,080

(22) PCT Filed: Jan. 26, 2018

(86) PCT No.: PCT/JP2018/002591
§ 371 (c)(1),
(2) Date: Aug. 2, 2019

(87) PCT Pub. No.: WO2018/143106
PCT Pub. Date: Aug. 9, 2018

(65) Prior Publication Data
US 2020/0003766 A1   Jan. 2, 2020

(30) Foreign Application Priority Data
Feb. 3, 2017 (JP) .............................. JP2017-018773

(51) Int. Cl.
*G01N 33/543* (2006.01)
*B01L 3/00* (2006.01)
(Continued)

(52) U.S. Cl.
CPC .......... *G01N 33/543* (2013.01); *B01L 3/5025* (2013.01); *C09K 11/07* (2013.01); *G01N 21/76* (2013.01); *B01L 2200/16* (2013.01)

(58) Field of Classification Search
CPC .... G01N 33/543; G01N 21/76; G01N 33/542; G01N 33/54366; G01N 33/54386;
(Continued)

(56) References Cited

U.S. PATENT DOCUMENTS 5,641,635 A   6/1997   Emmons et al.
6,090,568 A   7/2000   Belly et al.
(Continued)

FOREIGN PATENT DOCUMENTS

EP   0675362 A2   10/1995
JP   S62-103542 A   5/1987
(Continued)

OTHER PUBLICATIONS

Yoshida et al., "Examination of bilirubin," (History of Medical Examination) Modern Media, 59:119-124 (2013).
(Continued)

*Primary Examiner* — Christopher L Chin
(74) *Attorney, Agent, or Firm* — Morgan, Lewis & Bockius LLP

(57) ABSTRACT

The present disclosure relates to a device including a reagent portion in which a chemiluminescent indicator and a chemiluminescent substrate for the indicator are disposed, and a base on which the reagent portion is formed. The chemiluminescent indicator and the chemiluminescent substrate are disposed independently from each other in the reagent portion in such a manner that the chemiluminescent indicator and the chemiluminescent substrate can react with each other when a sample is supplied to the reagent portion. The present disclosure also relates to a remote diagnosis system including an imaging terminal for detecting a luminescent signal generated when a reagent is supplied to the device and an information processing unit for processing luminescent signal data obtained by the imaging terminal. The imaging
(Continued)

terminal and the information processing unit can bi-directionally communicate with each other via a network.

14 Claims, 5 Drawing Sheets

Specification includes a Sequence Listing.

(51) Int. Cl.
*C09K 11/07* (2006.01)
*G01N 21/76* (2006.01)

(58) Field of Classification Search
CPC ............ G01N 33/54393; G01N 21/763; B01L 3/5025; B01L 2200/16; C09K 11/07
USPC ......... 422/52, 408, 68.1, 420; 436/172, 136, 436/546, 805; 427/2.13; 435/962, 970, 435/7.9, 8
See application file for complete search history.

(56) References Cited

U.S. PATENT DOCUMENTS

| | | | |
|---|---|---|---|
| 6,246,525 B1 | 6/2001 | Ikami | |
| 2002/0022226 A1 | 2/2002 | Nakao et al. | |
| 2009/0268024 A1 | 10/2009 | Tsukuda et al. | |
| 2014/0194325 A1* | 7/2014 | Hitko | G01N 33/542 435/8 |
| 2016/0076079 A1 | 3/2016 | Encell et al. | |
| 2016/0115381 A1 | 4/2016 | Lee et al. | |
| 2016/0146794 A1* | 5/2016 | Johnsson | C12Q 1/66 435/174 |

FOREIGN PATENT DOCUMENTS

| | | | |
|---|---|---|---|
| JP | H03-282257 A | 12/1991 | |
| JP | H06-098030 B2 | 12/1994 | |
| JP | 2000-500568 A | 1/2000 | |
| JP | 2000-074837 A | 3/2000 | |
| JP | 3179673 B2 | 4/2001 | |
| JP | 2001-255328 A | 9/2001 | |
| JP | 2010-286467 A | 12/2010 | |
| JP | 2013-120120 A | 6/2013 | |
| JP | 2017-026635 A | 2/2017 | |
| WO | 97/19353 A1 | 5/1997 | |
| WO | 2007/076023 A2 | 7/2007 | |
| WO | 2010/064734 A1 | 6/2010 | |
| WO | WO-2015007317 A1 * | 1/2015 | ........... G01N 21/763 |

OTHER PUBLICATIONS

Yamada, "Analytical methods for food additives in foods," Bunseki (Analysis) Japan Food Chemical Research Foundation, 4: 296-301 (1997).
Saito et al., "Auto-Luminescent Genetically-Encoded Ratiometric Indicator for Real-Time Ca2+ Imaging at the Single Dell Level," PLOS One, 5: e9935 (2010).
Saito et al., "Luminescent proteins for high-speed single-cell and whole-body imaging," Nature Communications, 3:1262 (2012).
Suzuki et al., "Five colour variants of bright luminescent protein for real-time multicolour bioimaging," Nature Communications, 7: 13718 (2016).
Yang et al., "Coupling optogenetic stimulation with NanoLuc-based luminescence (BRET) Ca++ sensing," Nature Communications, 7: 13268 (2016).
Kumagai et al., "A Bilirubin-Inducible Fluorescent Protein from Eel Muscle," Cell, 153: 1602-1611 (2013).
Rodriguez et al., "A far-red fluorescent protein evolved from a cyanobacterial phycobiliprotein," Nature Methods, 13:763-769 (2016).
Shu et al., "Mammalian expression of infrared fluorescent proteins engineered from a bacterial phytochrome," Science, 324: 804-807 (2009).
Filonov et al., "Bright and stable near infra-red fluorescent protein for in vivo imaging," Nature Biotechnology, 29:757-761 (2011).
Drepper et al., "Reporter proteins for in vivo fluorescence without oxygen," Nature Biotechnology, 25:443-445 (2007).
Chapman et al., "The photoreversible fluorescent protein iLOV outperforms GFP as a reporter of plant virus infection," PNAS 105: 20038-20043 (2008).
Shu et al., "A Genetically Encoded Tag for Correlated Light and Electron Microscopy of Intact Cells, Tissues, and Organisms," PLOS Biology, 9: e1001041 (2011).
International Search Report issued in corresponding International Patent Application No. PCT/JP2018/002591 dated Apr. 3, 2018.
Extended European Search Report issued in corresponding European Patent Application No. 18748834.1 dated Feb. 11, 2020.

* cited by examiner

DEVICE AND DETERMINATION SYSTEM USING SAME

Sequence Listing Submission Via EFS-Web

A computer readable text file, entitled "SequenceListing.txt," created on or about Aug. 2, 2019 with a file size of about 8 kb contains the sequence listing for this application and is hereby incorporated by reference in its entirety.

TECHNICAL FIELD

The present disclosure relates to a device and a determination system that uses the device.

BACKGROUND ART

In recent years, there is need for a method by which not only biological materials but also substances contained in food, chemical substances, and the like are analyzed easily. Colorimetry is one example of a method of measuring these substances (for example, Non-patent Documents 1 and 2 etc.).

CITATION LIST

Non-Patent Documents

Non-Patent Document 1: Toshihiko Yoshida et al., MODERN MEDIA, Vol. 59, No. 5, 2013 [IGAKU KENSA NO AYUMI (History of Medical Examination)], 119-124

Non-Patent Document 2: Takashi Yamada, BUNSEKI (Analysis), No. 4, 296-301 (1997)

DISCLOSURE OF INVENTION

Problem to be Solved by the Invention

In measurement using colorimetry, there are cases where a special measuring apparatus is required for the measurement. For this reason, there is demand for novel means that allows a user himself/herself to perform measurement easily without using any special apparatus.

In one aspect, the present disclosure provides a device with excellent operability and portability and a determination system that uses the device.

Means for Solving the Problem

In one or more embodiments, the present disclosure relates to a device including: a reagent portion in which a chemiluminescent indicator and a chemiluminescent substrate for the indicator are disposed; and a base on which the reagent portion is formed, wherein the chemiluminescent indicator and the chemiluminescent substrate are disposed independently from each other in the reagent portion.

In one or more embodiments, the present disclosure relates to a determination system including: an imaging terminal for detecting a luminescent signal generated when a reagent is supplied to the device according to the present disclosure, and an information processing unit for processing luminescent signal data obtained by the imaging terminal, wherein the imaging terminal and the information processing unit can bi-directionally communicate with each other via a network.

Effects of the Invention

In one aspect, the present disclosure can provide a device with excellent operability and portability and a determination system that uses the device.

BRIEF DESCRIPTION OF DRAWINGS

FIG. 7A shows a chemiluminescence image taken with a color camera, and FIG. 7B shows a chemiluminescence image taken with a camera of a smartphone.

FIG. 8A shows chemiluminescence spectra. FIG. 8B is a graph showing the relationship between the dilution rate of the UnaG (CΔ0)-NLuc (NΔ1) fusion protein solution (detection reagent) and the ratio value (530 nm/460 nm) of peaks obtained from luminescence intensities.

FIG. 9A shows fluorescence spectra. FIG. 9B is a graph showing the relationship between the concentration of a UnaG protein solution (detection reagent) and the fluorescence intensity at the peak (530 nm).

DESCRIPTION OF THE INVENTION

Figure 1:
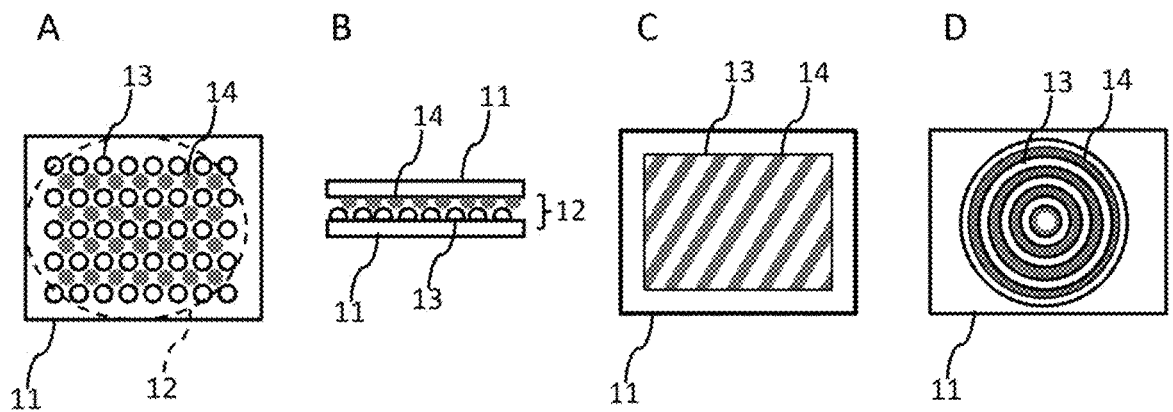
FIGS. 1A to 1D are schematic views showing examples of the arrangement (patterning) of a chemiluminescent indicator and a chemiluminescent substrate for the indicator in a device of the present disclosure.

The present disclosure is based on the finding that, by using a device in which a chemiluminescent indicator and a chemiluminescent substrate for the chemiluminescent indicator are disposed in such a manner that they react with each other when a sample is added dropwise to the device, a user himself/herself can measure a substance in the sample easily without using an excitation light source or a special apparatus for measurement.

The present disclosure is based on the finding that, by using a chemiluminescent indicator in which a chemiluminescent protein is fused to a protein that emits fluorescence by binding a substance in such a manner that resonance energy transfer can occur, a user himself/herself can measure the substance easily without using an excitation light source or a special apparatus for measurement.

The present disclosure is based on the finding that chemiluminescence obtained using the above-described chemiluminescent indicator can be detected by an imaging unit, such as a mobile terminal (smart phone, tablet terminal, etc.) or a digital camera, owned by a user himself/herself, and quick measurement, determination, diagnosis, or the like becomes possible by transmitting through a communication line the thus-detected data to an examination institute or the like or to an application installed on the mobile terminal.

[Device]

In one or more embodiments, the device according to the present disclosure includes a reagent portion in which a chemiluminescent indicator and a chemiluminescent substrate for the indicator are disposed and a base on which the reagent portion is formed.

In the reagent portion, at least the chemiluminescent indicator and the chemiluminescent substrate for the chemiluminescent indicator are disposed.

In one or more embodiments, the chemiluminescent indicator may be an indicator that generates a luminescent signal by binding to or acting on an analyte. In one or more embodiments, the chemiluminescent indicator may be a fusion protein in which an acceptor protein that can emit luminescence by binding to or acting on an analyte and a donor protein that can excite the luminescence emitted by the acceptor protein with its luminescence energy. In one or more embodiments, the chemiluminescent indicator can be selected as appropriate according to an analyte. Specific examples of the chemiluminescent indicator will be described below.

In one or more embodiments, the chemiluminescent substrate may be a substance that can act as a substrate for a chemiluminescent protein in the chemiluminescent indicator and also emits luminescence. In one or more embodiments, the chemiluminescent substrate is a substance that acts as a substrate for a donor protein. In one or more embodiments, the chemiluminescent substrate can be determined as appropriate according to the chemiluminescent indicator or the donor protein.

In the device of the present disclosure, the chemiluminescent indicator and the chemiluminescent substrate are disposed independently from each other. In one or more embodiments, the chemiluminescent indicator and the chemiluminescent substrate are disposed in such a manner that, when a sample is supplied to the reagent portion in which they are disposed, a luminescent signal can be generated as a result of a reaction between the chemiluminescent indicator and the chemiluminescent substrate. Accordingly, when a sample is supplied to the reagent portion, the chemiluminescent indicator and the chemiluminescent substrate come into contact with each other (they are mixed together) and an analyte in a reagent binds to or acts on the chemiluminescent indicator, whereby a luminescent signal can be generated. In one or more embodiments, the device according to the present disclosure with such a configuration preferably can exhibit effects that it has a higher signal-to-noise ratio and that the necessity of using a special measuring apparatus or special measuring equipment is eliminated because it is not necessary to use excitation light. Moreover, according to the device of the present disclosure, in one or more embodiments, a user can detect a generated luminescent signal by taking an image of the luminescent signal with an imaging unit, such as a mobile terminal, owned by the user himself/herself, and also, measurement, determination, diagnosis, or the like can be performed quickly using data obtained from the image taken by the user.

In the present disclosure, the state of being "disposed independently from each other" may be, in one or more embodiments, a state where a chemiluminescent indicator and a chemiluminescent substrate are disposed in such a manner that they do not react with each other unless liquid such as a sample comes into contact with them. In one or more embodiments, the state of being disposed independently from each other may be such that a chemiluminescent indicator and a chemiluminescent substrate that are adjacent to each other are physically separated from each other. In one or more embodiments, the state of being disposed independently from each other may encompass a state where a chemiluminescent indicator and a chemiluminescent substrate are disposed in contact with each other as long as the chemiluminescent indicator and chemiluminescent substrate are in a state where they do not react with each other (e.g., they are in a dry state).

In one or more embodiments, the chemiluminescent indicator and the chemiluminescent substrate may be disposed by means of patterning. In one or more embodiments, they may be patterned into dot shapes, linear shapes, circular shapes, or the like. From the viewpoint of increasing the contact ratio between the chemiluminescent indicator and the chemiluminescent substrate to obtain a higher luminescent signal, patterning is preferably such that, in one or more embodiments, the chemiluminescent indicator and the chemiluminescent substrate are disposed alternately so as to form a mosaic pattern. Fine patterning is preferable because the repeatability can be improved.

In the device of the present disclosure, the reagent portion is formed on the base. In one or more embodiments, the reagent portion may be formed on the same plane of one base, or may be formed so as to be sandwiched between two bases.

FIGS. 1A to 1D show non-limiting examples of the patterning shape. In FIG. 1A, a reagent portion 12 is formed by disposing a chemiluminescent reagent 13 and a chemiluminescent substrate 14 that are both patterned into dot shapes alternately so as to form a mosaic pattern on one base 11. In FIG. 1B, a reagent portion 12 is formed by patterning a chemiluminescent reagent 13 into dot shapes on one surface of one base 11 and a chemiluminescent substrate 14 into dot shapes on one surface of another base 11, and disposing the two bases 11 such that the surface on which the chemiluminescent reagent 13 is patterned and the surface on which the chemiluminescent substrate 14 is patterned face each other. In FIGS. 1C and 1D, a reagent portion 12 is formed by patterning a chemiluminescent reagent 13 and a chemiluminescent substrate 14 into linear shapes or circular shapes on one base 11.

In one or more embodiments, the chemiluminescent indicator and the chemiluminescent substrate are preferably in a dry state from the viewpoint of reducing the possibility that the chemiluminescent indicator and the chemiluminescent substrate may react with each other before supplying a sample.

The material of the base is not particularly limited, and in one or more embodiments, it may be paraffin, a fluorine-based material such as Teflon®, glass, polypropylene, woven fabric, non-woven fabric, paper, or the like. In one or more embodiments, the material of the base is preferably hydrophobic, because a high luminescent signal can be detected.

[Chemiluminescent Indicator]

The term "chemiluminescent indicator" as used in the present disclosure refers to a chemiluminescent indicator that involves generation of chemiluminescence or chemiluminescence energy at least in part of a process in which the chemiluminescent indicator generates a luminescent signal.

In one or more embodiments, the chemiluminescent indicator may be a fusion protein that includes a chemiluminescent protein moiety. In one or more embodiments, the chemiluminescent indicator may be a known chemiluminescent indicator, or may be a chemiluminescent indicator that is currently under development or may be developed in the future.

In one or more embodiments, the chemiluminescent indicator may be, for example, a chemiluminescent indicator that utilizes Førster resonance energy transfer (FRET) caused when the chemiluminescent indicator binds to or acts on an analyte.

In one or more embodiments, examples of the chemiluminescent indicator that utilizes FRET include: chemiluminescent calcium ion indicators (K Saito et al., PLoS ONE, 5: e9935, 2010, K Saito et al., Nature, Communications, 3, 1262, 2012, K Suzuki et al, Nature, Communications, 7, 13718, 2016, Yang J et al., Nature Communications, 7, 13268, 2016); and chemiluminescent ATP indicators and chemiluminescent cAMP indicators (K Saito et al., Nature, Communications, 3, 1262, 2012).

Other examples of the chemiluminescent indicator include, in one or more embodiments, a fusion protein (C) in which a protein (A) capable of binding an analyte, such as a biological material, in a sample and a chemiluminescent protein (B) are fused together. The chemiluminescent indicator is based on the finding of the present inventors that, by fusing a chemiluminescent protein to a protein that emits fluorescence upon binding a biological material in such a manner that resonance energy transfer can occur, the necessity of using an excitation light source for observation is eliminated, and also, two wavelengths of measurement light can be used, and accordingly, quantification of the analyte can be performed easily. In one or more embodiments, the "protein (A) capable of binding an analyte" may be a protein (A1) that can emit fluorescence in a state where the analyte is bound thereto or a protein (A2) capable of binding an autofluorescent molecule as the analyte.

An example of the chemiluminescent indicator used in the device of the present disclosure will be described specifically with reference to an example where an analyte to which a protein (A) in a fusion protein (C) can bind is a biological material.

[Protein (A) Capable of Binding Biological Material]

The "protein (A) capable of binding a biological material" in the fluorescent protein (C) in such an example may be a protein (A1) that can emit fluorescence in a state where a biological material is bound thereto or a protein (A2) capable of binding an autofluorescent molecule as the biological material.

In one or more embodiments, the protein (A1) that can emit fluorescence in a state where a biological material is bound thereto may be a protein that is non-fluorescent when it is in the apo form and becomes fluorescent when it turns to the holo form upon binding a biological material that is a ligand. In one or more embodiments, the protein (A1) may be a UnaG protein. In one or more embodiments, the protein (A1) may be smURFP, IFP, or iRFP.

A UnaG protein specifically binds to indirect bilirubin and emits green light when irradiated with cyan excitation light (Kumagai et al., Cell 2013, 153, 1602-1611). UnaG has very high binding ability to indirect bilirubin (dissociation constant=98 pM). For sequence information of UnaG, reference can be made to UniProtKB/Swiss-Prot: P0DM59.1 or GenBank: AB763906.1 (as of August 2016). By using a UnaG protein as the protein (A1), indirect bilirubin can be detected, for example.

smURFP is an abbreviation for small ultra red fluorescent protein, and refers to a protein that exhibits red fluorescence upon binding biliverdin, which is a metabolite of hemoglobin (Rodriguez et al., Nature Methods, 2016, 13, 763-769).

IFP is an abbreviation for infrared-fluorescent protein, and refers to a protein that exhibits red fluorescence upon binding biliverdin (Shu X, et al., Science 2009, 324 (5928), 804-8-7).

iRFP is an abbreviation for near-infrared fluorescent protein, and refers to a protein that exhibits red fluorescence upon binding biliverdin (Filonov G S, et al., Nat Biotech 2011, 29 (8), 757-761).

By using any of these smURFP, IFP, and iRFP as the protein (A1), biliverdin can be detected, for example.

The protein (A1) may be a variant of the UnaG protein or a variant of smURFP, IFP, or iRFP. The variant of the UnaG protein or the variant of smURFP, IFP, or iRFP may include a mutation(s) such as deletion, addition, and/or substitution to the extent that the variant can maintain its properties of being converted to the holo form and becoming fluorescent upon binding bilirubin or biliverdin as a ligand. The number of mutated amino acids is not particularly limited. In one or more embodiments, the number of mutated amino acids may be 1 to 4, 1 to 3, 1 to 2, or 1, or alternatively, the amino acid sequence of the variant may have a sequence identity of at least 90% or more, 91% or more, 92% or more, 93% or more, 94% or more, 95% or more, 96% or more, 97% or more, 98% or more, 99% or more, or 99.5% or more. Non-limiting examples of the mutation include deletion of the fusion moiety (C-terminal or N-terminal) with the protein (B) in the fusion protein (C).

The protein (A2) capable of binding an autofluorescent molecule as the biological material refers to a protein that becomes fluorescent upon binding the autofluorescent molecule. The autofluorescent molecule may be flavin mononucleotide (FMN). In one or more embodiments, the protein (A2) capable of binding the autofluorescent molecule (FMN) may be FbFP, an iLOV protein, or a mini-SOG protein.

FbFP is an abbreviation for flavin mononucleotide (FMN)-based fluorescent protein, and refers to a fluorescent protein derived from a blue-light receptor of bacteria (Drepper T., et al., Nat Biotech. 2007, 25(4) 443-445).

An iLOV protein is a protein with improved fluorescent properties obtained by modifying a fluorescent protein derived from a light, oxygen, or voltage-sensing (LOV) domain of a plant blue-light receptor phototropin (Chapman S., et al., PNAS 2008, 105 (50) 20038-43).

A mini-SOG protein is an abbreviation for mini singlet oxygen generator, and refers to a fluorescent protein derived from phototropin 2 in *Arabidopsis* (Shu X., et al., PLoS Biol. 2011, 9(4)).

The protein (A2) may be a variant that includes a mutation(s) such as deletion, addition, and/or substitution to the extent that the variant can bind the autofluorescent molecule. The number of mutated amino acids may be within the above-described ranges.

[Chemiluminescent Protein (B)]

The chemiluminescent protein (B) can excite fluorescence or autofluorescence of the protein (A) with its luminescence energy. According to a detection method of the present disclosure, in which the fusion protein (C) including the chemiluminescent protein (B) with such a configuration is used as a detection reagent, quantitative measurement of a biological material can be performed without using an excitation light source for observation. The chemiluminescent protein (B) may be a photoprotein (luciferase) that can serve as a resonance energy transfer donor and can excite fluorescence of the protein (A) at the time of resonance energy transfer. It is preferable that the protein (A) and the protein (B) exhibit different luminescent colors, because whether the detection target has been detected can be determined with reference to the luminescent color.

The resonance energy transfer is known as Förster resonance energy transfer (FRET) or bioluminescence resonance energy transfer (BRET). The protein (B) can be selected according to the absorption wavelength of the protein (A1) or the absorption wavelength of the autofluorescent molecule that binds to the protein (A2). Examples of the protein (B) include known photoproteins, such as firefly luciferase, aequorin, bacterial luciferase, and variants thereof.

When the protein (A) is UnaG, the protein (B) may be, in one or more embodiments, luciferase that uses a coelenterazine compound as a chemiluminescent substrate. In one or more embodiments, the luciferase may be NLuc.

The protein (B) may be a variant of known luciferase. The variant of luciferase may include a mutation(s) such as deletion, addition, and/or substitution to the extent that the variant can maintain its properties of emitting light upon binding luciferin. The number of mutated amino acids is not particularly limited. In one or more embodiments, the number of mutated amino acids may be 1 to 4, 1 to 3, 1 to 2, or 1, or alternatively, the amino acid sequence of the variant may have a sequence identity of at least 90% or more, 91% or more, 92% or more, 93% or more, 94% or more, 95% or more, 96% or more, 97% or more, 98% or more, 99% or more, or 99.5% or more. Non-limiting examples of the mutation include deletion of the fusion moiety (C-terminal or N-terminal) with the protein (A) in the fusion protein (C).

[Linker]

In the fusion protein (C), the protein (A) and the protein (B) may be linked via a linker. The linker may be selected so as to enhance the efficiency of resonance energy transfer from the protein (B) to the protein (A). In one or more embodiments, the length of the linker may be 1 to 10, 1 to 5, 2 to 4, or 2 to 3 amino acid residues.

When the protein (A) is UnaG, the linker may be GT, DD, GTG, GTGG, or the like in one or more embodiments. Among them, from the viewpoint of luminescence efficiency, DD, GTG, or GTGG is preferable and GTG is more preferable.

The order in which the protein (A) and the protein (B) are fused in the fusion protein (C) is not particularly limited, and either the protein (A) or the protein (B) may be on the N-terminal side of the fusion protein (C). In one or more embodiments, the fusion protein (C) may have a tag protein fused to the N-terminus or the C-terminus thereof.

According to the above-mentioned configuration of the fusion protein (C), the luminescent color of the protein (A) tends to be exhibited in the presence of both a biological material acting as a substrate for the protein (A) and luciferin acting as a substrate for the protein (B), and the luminescent color of the protein (B) tends to be exhibited more strongly as the amount of the biological material acting as the substrate for the protein (A) is reduced. Accordingly, the fusion protein (C) enables detection/measurement of the biological material.

In one or more embodiments, the device of the present disclosure can also be referred to as an analysis device or analysis chip for analyzing a specific detection target. In one or more embodiments, in the case where an analyte is a biological material, the device of the present disclosure can also be referred to as a biodevice or biochip.

The analyte to be detected by the device of the present disclosure is not particularly limited, and in one or more embodiments, the analyte may be a biological material in a biological sample, an allergen or a harmful substance in food, a contaminant or a harmful substance in the natural environment such as river water or seawater, a pathogen, or the like. In one or more embodiments, the sample may be a biological sample, a food, or the like.

The biological sample is a sample containing the biological material derived from a living organism, and is preferably in a liquid state. Examples of such a biological sample include, but not particularly limited to, body fluid samples such as whole blood, serum, plasma, and urine. The biological sample in the present disclosure may be diluted and/or pretreated as necessary. Needless to say, a detection method according to the present disclosure is also applicable to measurement of samples other than the above-described "biological sample". For example, the detection method is also applicable to a standard sample of a biological material as an analyte, i.e., to a control sample used for the measurement.

In one or more embodiments, the biological material may be a low molecular weight compound in a living organism, a metabolite obtained by degradation, a nucleic acid, a sugar, a peptide, a protein, a cell, a microorganism, or the like.

[Production Method of Device]

The production method according to the present disclosure is, in one or more embodiments, a method of producing the device of the present disclosure. The production method of the present disclosure includes patterning a chemiluminescent indicator and a chemiluminescent substrate for the chemiluminescent indicator on a base in such a manner that the chemiluminescent indicator and the chemiluminescent substrate are disposed independently from each other.

In one or more embodiments, patterning of the chemiluminescent indicator and the chemiluminescent substrate can be performed by disposing them independently from each other in such a manner that, when a sample is supplied to a portion where they are disposed, the chemiluminescent indicator and the chemiluminescent substrate come into contact with each other (they are mixed together), whereby a luminescent signal can be generated.

In one or more embodiments, the patterning method may be placing a solution of the chemiluminescent indicator and a solution of the chemiluminescent substrate so as to form a predetermined pattern and then drying the solutions. In one or more embodiments, the patterning may be performed using a known technique such as the use of an inkjet printer.

The chemiluminescent indicator, the chemiluminescent substrate, the base, the patterning shape, and the like are the same as those described above in connection with the device of the present disclosure.

[Detection Method]

A detection method according to the present disclosure is a method of detecting an analyte in a sample using the device of the present disclosure.

In one or more embodiments, the detection method of the present disclosure includes supplying a sample to the reagent portion of the device of the present disclosure and detecting a luminescent signal generated as a result of supplying the sample. The device of the present disclosure does not require excitation light. Accordingly, in one or more embodiments, detection of the luminescent signal can be performed using an imaging unit such as a mobile terminal (smartphone or the like) or a digital camera.

In one or more embodiments, the detection method of the present disclosure can be performed at room temperature or ambient temperature. In one or more embodiments, the time elapsing from the supply of the sample until the observation may be around a few seconds to a few minutes, or around a few seconds to one minute.

One or more non-limiting embodiments of the detection method of the present disclosure will be described with reference to an example where the detection method is performed using a fusion protein (C) in which a protein (A) capable of binding a biological material and a chemiluminescent protein (B) are fused together.

When a sample is added to a reagent portion in which the fusion protein (C) and a substrate for the protein (B) are disposed, luminescence is emitted. Using this luminescent signal as an index, the presence or absence of a biological material that has bound to a protein (A) can be determined. Basically, the luminescent color of the protein (A) is exhibited in the presence of the biological material, and the luminescent color of the protein (B) is exhibited in the absence of the biological material.

According to the detection method in this example, in one or more embodiments, the luminescent color of the sample changes in a manner dependent on the concentration of the biological material. As the concentration of the biological material increases, the luminescent color of the sample changes from the luminescent color of the protein (B) to the luminescent color of the protein (A). That is, the luminescence intensity ratio between the protein (A) and the protein (B) in a luminescent signal can be correlated with the concentration of the biological material.

Therefore, the detection method in this example enables quantitative measurement of the concentration of the biological material on the basis of the luminescent signal, regardless of the amount of the sample. From the viewpoint of enabling the quantitative measurement, the molar concentration of the fusion protein (C) to be brought into contact with (to be mixed with) the sample is preferably within a range around the $K_d$ value.

In one or more embodiments, the detection method according to the present disclosure may include a step of quantitatively calculating the concentration of the biological material from the luminescent signal of the sample.

[Determination Method]

In another aspect, the present disclosure relates to a method of determining the concentration of an analyte in a sample, including: determining the concentration of the analyte in the sample on the basis of luminescent signal data obtained by the detection method according to the present disclosure.

As described above, the luminescence intensity ratio between the proteins (A) and (B) in the luminescent signal obtained by the detection method according to the present disclosure can change in a manner dependent on the concentration of the biological material. Therefore, the concentration of the biological material can be determined from the information on the fusion protein (C) used for the detection and the luminescent signal The luminescent signal data can be easily captured and transmitted/received using a color detector such as a color camera of a mobile terminal (smartphone or the like). Accordingly, the concentration of the biological material can be grasped easily.

[Determination System]

In another aspect, the present disclosure relates to a determination system that uses the device of the present disclosure (the determination system of the present disclosure). The determination system of the present disclosure includes an imaging terminal for detecting a luminescent signal generated when a sample is supplied to the device and an information processing unit for processing luminescent signal data obtained by the imaging terminal. In the determination system of the present disclosure, the imaging terminal and the information processing unit may be configured such that they can bi-directionally communicate with each other via a network. The determination system of the present disclosure may further include a communication terminal that can bi-directionally communicate with the information processing unit via a network.

According to the determination system of the present disclosure, in one or more embodiments, a user can obtain the result of analysis, determination, or diagnosis by experts quickly and easily without going to any special examination institute or the like, and besides, regardless of where the user is and even when the user is at a remote location. In one or more embodiments, the determination system of the present disclosure can be used as a remote analysis system, a remote determination system, or a remote diagnosis system.

In one or more embodiments, the imaging terminal may be a general-purpose image reading apparatus or the like. The image reading apparatus is not particularly limited, and in one or more embodiments, examples thereof include a mobile terminal such as a smartphone or a tablet terminal, a digital camera, and a CCD camera. In one or more embodiments, the imaging terminal may be a mobile terminal such as a smartphone or a tablet terminal, because measurement, receipt of the result of determination, and the like can be performed quickly.

In one or more embodiments, detection of a luminescent signal can be performed by taking an image of a luminescent signal generated when a sample is supplied to the device of the present disclosure with the imaging terminal. In one or more embodiments, from the viewpoint of improving the measurement accuracy, the detection of the luminescent signal can be performed by attaching an attachment to a camera portion of the imaging terminal and placing in the attachment the device of the present disclosure to which the sample has been supplied.

In one or more embodiments, the detected luminescent signal can be transmitted to the information processing unit by the imaging terminal that has detected the luminescent signal. In one or more embodiments, the transmission to the information processing unit may be performed using an application installed on the imaging terminal. Alternatively, the detected luminescent signal may be transmitted to the information processing unit by a communication terminal that is different from the imaging terminal. In one or more embodiments, the communication terminal may be, for example, a personal computer with a communication function.

In one or more embodiments, the information processing unit stores luminescent signal data on luminescent signals generated by a chemiluminescent indicator used for an analyte and information associated with reference luminescent signal data, and can make a determination on the basis of the data and information described above and luminescent signal data detected by the imaging terminal. In one or more embodiments, the information processing unit performs operations including comparing the transmitted luminescent signal data with the reference luminescent signal data and transmitting the obtained diagnosis result to the imaging terminal.

The present disclosure further relates to one or more non-limiting embodiments to be described below.

[1] A device including:
a reagent portion in which a chemiluminescent indicator and a chemiluminescent substrate for the indicator are disposed; and
a base on which the reagent portion is formed,
wherein the chemiluminescent indicator and the chemiluminescent substrate are disposed independently from each other in the reagent portion.

[2] The device according to [1],
wherein the chemiluminescent indicator and the chemiluminescent substrate are disposed in such a manner that the chemiluminescent indicator and the chemiluminescent substrate can react with each other when a sample is supplied to the reagent portion.

[3] The device according to [2],
wherein the chemiluminescent indicator is a fusion protein (C) in which a protein (A) capable of binding an analyte in the sample and a chemiluminescent protein (B) are fused together, and
the protein (A) and the protein (B) are linked in such a manner that resonance energy transfer can occur.

[4] The device according to [3],
wherein the substrate is a substrate for the chemiluminescent protein (B).

[5] The device according to [3] or [4],
wherein the protein (A) is either a protein (A1) that can emit fluorescence in a state where the analyte is bound thereto or a protein (A2) capable of binding an autofluorescent molecule as the analyte, and
the protein (B) can excite fluorescence or autofluorescence of the protein (A) with its luminescence energy.

[6] A determination system including:
an imaging terminal for detecting a luminescent signal generated when a sample is supplied to the device according to any one of [1] to [5], and
an information processing unit for processing luminescent signal data obtained by the imaging terminal,
wherein the imaging terminal and the information processing unit can bi-directionally communicate with each other via a network.

[7] A method of producing a device, the method including:
patterning a chemiluminescent indicator and a chemiluminescent substrate for the indicator on a base in such a manner that the chemiluminescent indicator and the chemiluminescent substrate are disposed independently from each other.

Hereinafter, the present disclosure will be described in further detail by way of examples. However, these examples are merely illustrative, and the present disclosure is not limited to the following examples.

EXAMPLES

Experimental Example

1. Gene Construction of Fusion Proteins (Chemiluminescent Indicators)

C-terminal deletion mutants of a wild-type UnaG were amplified using the following primers each having a BamHI restriction enzyme site added to the N-terminus and a KpnI restriction enzyme site added to the C-terminus.

```
Forward primer:
                                    (SEQ ID NO: 1)
       CGCGGATCCGGGTGGTTCTGGTATGG Reverse primer 0:
                                    (SEQ ID NO: 2)
(CΔ0)  GCTGGTACCTTCCGTCGCCCTCCG Reverse primer 1:
                                    (SEQ ID NO: 3)
(CΔ1)  GCTGGTACCCGTCGCCCTCCGGTA Reverse primer 2:
                                    (SEQ ID NO: 4)
(CΔ2)  GCTGGTACCCGCCCTCCGGTAGCT Reverse primer 3:
                                    (SEQ ID NO: 5)
(CΔ3)  GCTGGTACCCCTCCGGTAGCTGCG Reverse primer 4:
                                    (SEQ ID NO: 6)
(CΔ4)  GCTGGTACCCCGGTAGCTGCGCAC
```

N-terminal deletion mutants of a wild-type NLuc were amplified using the following primers each having a KpnI restriction enzyme site added to the N-terminus and an EcoRI restriction enzyme site added to the C-terminus.

```
Forward primer 1:
                                    (SEQ ID NO: 7)
(NΔ1)  GCCGGTACCGTCTTCACACTCGAAGATTTCG Forward primer 2:
                                    (SEQ ID NO: 8)
(NΔ4)  GCCGGTACCCTCGAAGATTTCGTTGGGGAC Forward primer 3:
                                    (SEQ ID NO: 9)
(NΔ5)  GCCGGTACCGAAGATTTCGTTGGGGACTGGC Reverse primer:
                                    (SEQ ID NO: 10)
       ATGAATTCTTACGCCAGAATGCGTTCGCACAG
```

DNA fragments amplified by polymerase chain reaction (PCR) were extracted using a phenol-chloroform extraction method. The DNA fragments of UnaG were treated with restriction enzymes BamHI and KpnI. The DNA fragments of NLuc were treated with restriction enzymes KpnI and EcoRI. After agarose gel electrophoresis, bands were excised from the gel and purified (QIAEX2, QIAGEN). pRSET$_B$ vectors that had been treated with restriction enzymes BamHI and EcoRI were ligated to the thus-purified respective fragments, which were then transformed into the JM109 (DE3) strains. Thereafter, the JM109 (DE3) strains were cultured at 37° C. overnight on LB agar media prepared in 10-cm dishes.

2. Screening

The agar media in which colonies were formed were placed at room temperature. 4 mL of a solution containing bilirubin at a final concentration of 10 μM was added to 1% low-melting agarose gel that had been cooled to near room temperature, and the resultant mixture was poured onto the agar media and allowed to solidify at room temperature. Subsequently, a 10 μM Coelenterazine-h solution was poured onto the gel. Immediately after adding the solution, color images of the colonies were taken with a single-lens reflex camera (Sony α7) placed in a dark box. Ratio images were created from green channel (luminescence of UnaG) images and blue channel (luminescence of NLuc) images of the RGB images, and the colonies exhibited high ratio values were picked up. Next, the colonies thus picked up were cultured in LB media containing 10 μM bilirubin and 100 μg/mL Ampicillin at 23° C. for 60 hours on a 96-well plate. 10 μM coelenterazine was added to the culture solutions, and chemiluminescence spectra were measured using a spectrophotofluorometer (FV7000) or a plate reader. The chemiluminescence spectra were normalized at a wavelength of 450 nm, and screening was performed on the basis of a relative value (ratio value) at a wavelength of 525 nm.

Figure 2:
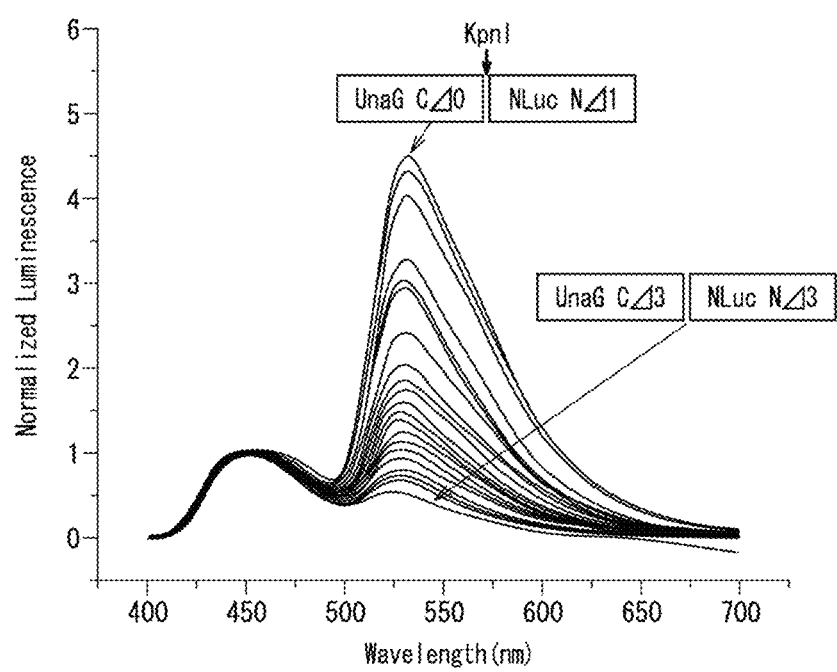
FIG. 2 shows chemiluminescence spectra of various UnaG-NLuc fusion proteins with C-terminal/N-terminal deletion mutations. UnaG (CΔ0)+NLuc (NΔ1) exhibited the highest FRET efficiency.

As a result of screening proteins obtained by fusing the C-terminal deletion mutants of UnaG and the N-terminal deletion mutants of NLuc at the KpnI site, the combination of UnaG (CΔ0) and NLuc (NΔ1) (hereinafter referred to as "UnaG (CΔ0)-NLuc (NΔ1) fusion protein") exhibited the highest Førster resonance energy transfer (FRET) efficiency (FIG. 2). The base sequence of this UnaG (CΔ0)-NLuc (NΔ1) fusion protein is represented by SEQ ID NO: 11, and the amino acid sequence of the same is represented by SEQ ID NO: 12.

3. Optimization of Linker Sequence in Fusion Protein

Two residues (GT) constituting a sequence at the junction of UnaG and NLuc, were substituted with random sequences by inverse PCR. The following primers were used.

```
Forward primer:
                                    (SEQ ID NO: 13)
NNKNNKGTCTTCACACTCGAAGATTTC Reverse primer:
                                    (SEQ ID NO: 14)
TTCCGTCGCCCTCCGGTAGCTG
```

The full-length sequences including vector sequences were amplified, and then treated with a restriction enzyme DpnI to treat template plasmids. After ligation, they were transformed into the JM109 (DE3) strains, which were then cultured at 37° C. overnight on LB agar media prepared in 10-cm dishes. Colonies expressed were subjected to screening in the manner described in the above item 2.

4. Insertion of Linker Sequences into Fusion Proteins

Linker sequences were inserted after the sequence (GT) at the junction of UnaG and NLuc by inverse PCR. The following primers were used.

```
Forward primer (G):
                                    (SEQ ID NO: 15)
GGCGTCTTCACACTCGAAGATTTC Forward primer (GG):
                                    (SEQ ID NO: 16)
GGCGGCGTCTTCACACTCGAAGATTTC Forward primer (GGS):
                                    (SEQ ID NO: 17)
GGCGGCAGCGTCTTCACACTCGAAGATTTC Reverse primer:
                                    (SEQ ID NO: 18)
GGTACCTTCCGTCGCCCTC
```

The full-length sequences including the vector sequences were amplified by PCR, and then treated with a restriction enzyme DpnI to treat template plasmids. After ligation, they were transformed into the JM109 (DE3) strains, which were then cultured at 37° C. overnight on LB agar media prepared in 10-cm dishes. Colonies expressed were subjected to screening in the manner described in the above item 2.

Figure 3:
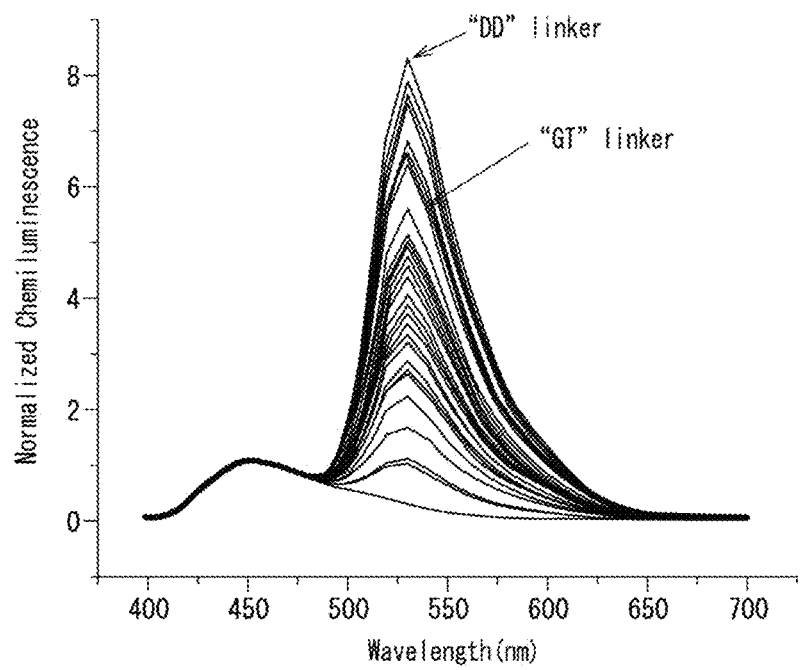
FIG. 3 shows chemiluminescence spectra obtained when various mutations were inserted to a linker sequence. As compared with a wild-type chemiluminescent bilirubin indicator with the linker sequence (GT), a mutant obtained by substituting the sequence (GT) with a DD sequence exhibited the largest change in FRET efficiency.

As a result of the linker sequence optimization by the insertion of random mutations, the (DD) sequence exhibited a large change in FRET efficiency as compared with the wild-type linker sequence (GT) (FIG. 3). Furthermore, examination on the FRET efficiencies of the chemiluminescent bilirubin indicators to which the flexible linkers had been added revealed that the chemiluminescent bilirubin indicator with the (GTG) sequence exhibited the highest FRET efficiency.

5. Purification of Protein

The J JM109 (DE3) strain transformed with the UnaG (CΔ0)-NLuc (NΔ1) fusion protein was cultured at 23° C. for 60 hours in 200 mL of LB medium containing 100 μg/mL Carvenisillin solution. After harvesting, the $E.\ coli$ cells were disrupted by the French press method and purified by affinity chromatography using a Ni-NTA column (QIAGEN). Furthermore, in order to remove excess imidazole, a gel filtration column (PD-10, GE HealthCare) was used. The protein concentration was measured by the Bradford method.

6. Preparation of Lyophilized Samples

500 μL of the purified UnaG (CΔ0)-NLuc (NΔ1) fusion protein was added to a 15-mL Falcon tube and frozen with liquid nitrogen. Thereafter, a powder of the protein solution was obtained by a lyophilizer. The powder was stored at room temperature.

Figure 4:
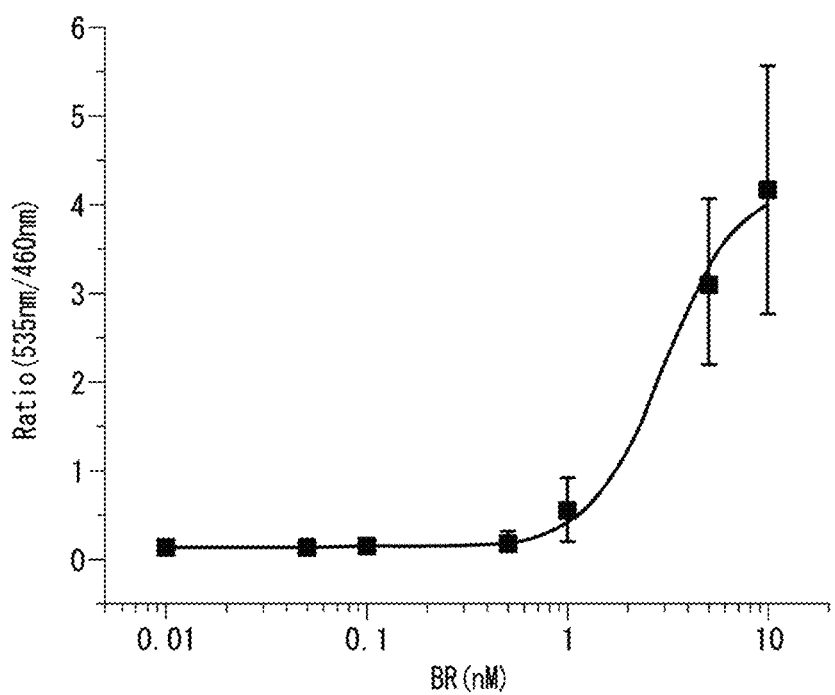
FIG. 4 shows a titration curve of the wild-type chemiluminescent bilirubin indicator. Mean values of measured values obtained by three independent measurements were plotted, and then fitted as per the Hill equation. The $K_d$ value was 3.05 nM.

7. Measurement of Titration Curve 0.01 nM, 0.05 nM, 0.1 nM, 0.5 nM, 1 nM, 2.5 nM, 5 nM, or 10 nM bilirubin solution and Coelenterazine-h at a final concentration of 5 μM were mixed with the UnaG (CΔ0)-NLuc (NΔ1) fusion protein at a final concentration of 5 nM, and luminescence spectra were measured using a multichannel spectroscope (PMA-12, manufactured by Hamamatsu Photonics K.K.) or a plate reader. FIG. 4 shows an example of the result obtained. Mean values of measured values obtained by three independent measurements were plotted, and then fitted as per the Hill equation. The $K_d$ value was 3.05 nM.

Figure 5:
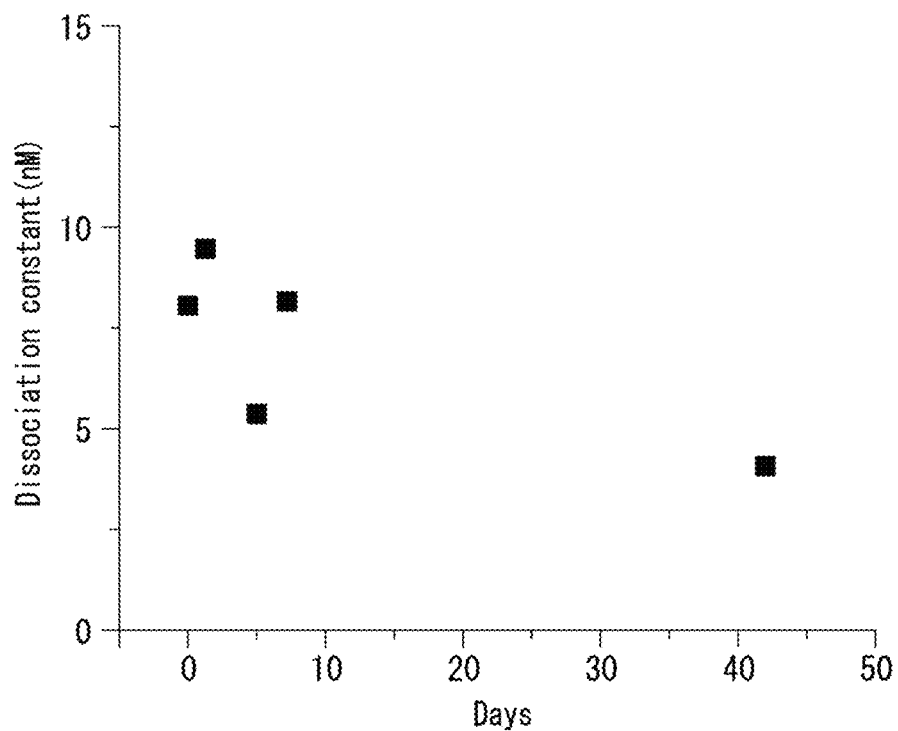
FIG. 5 shows change in bilirubin affinity (dissociation constant, $K_d$ value) of a lyophilized sample stored at room temperature.

After the preparation of the lyophilized samples, in order to investigate how long the activity is maintained, the lyophilized samples that had been dissolved in water were stored at room temperature every few days, and the affinity for bilirubin was measured according to the method described in the above item 7. As a result, it was found that the activity was maintained although the affinity varied to some extent (FIG. 5).

8. Measurement Using Smartphone

Bilirubin solution at a final concentration of 10 nM, 20 nM, 30 nM, 40 nM, 50 nM, 100 nM, or 250 nM and Coelenterazine-h at a final concentration of 5 μM were mixed with the fusion protein at a final concentration of 50 nM on a 96 multi-well plate, and the resultant mixtures were subjected to measurement using an application (Manual-Custom exposure camera) installed on an iPhone® 6 with ISO set to 1500 and an exposure time set to 0.5 seconds.

Figure 6:
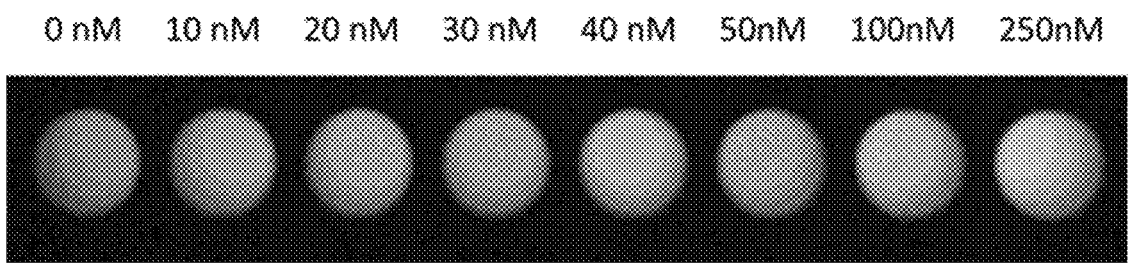
FIG. 6 shows a chemiluminescence image, taken with a smartphone, of solutions containing the wild-type chemiluminescent bilirubin indicator and various concentrations of bilirubin on a 96-well plate.

Color images of the solutions containing the fusion protein and the bilirubin solutions at the various concentrations prepared on the multi-well plate were taken. As a result, the state where the color of the solutions changed from blue to green in a manner dependent on the bilirubin concentration was successfully recorded (FIG. 6). As can be seen in FIG. 6, when the bilirubin concentration was 0 nM, the color of the solution was the luminescent color of the chemiluminescent protein (cyan). As the bilirubin concentration increased, the luminescent color changed toward the luminescent color of UnaG (green). According to an example of the explanation on the state of the color change using RGB, the luminescent colors changed as follows: 0 nM (56, 133, 204), 10 nM (79, 157, 215), 20 nM (96, 169, 209), 30 nM (101, 164, 194), 40 nM (119, 179, 189), 50 nM (123, 169, 156), 100 nM (154, 187, 111), and 250 nM (158, 191, 107).

If there is a correlation as shown in FIG. 6, the bilirubin concentration can be calculated from the luminescence data (luminescent color).

Example 1

Figure 7:
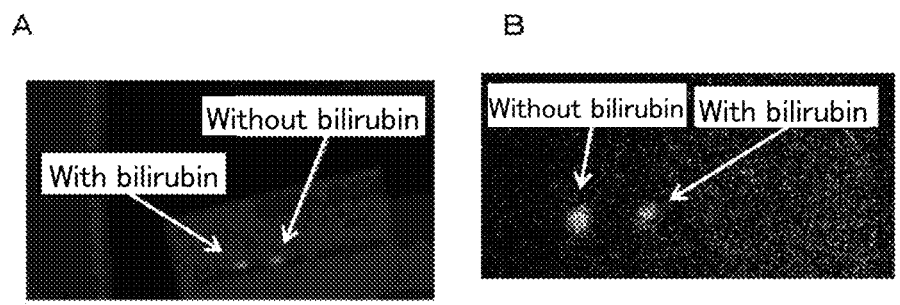
FIGS. 7A and 7B show chemiluminescence images, taken with cameras, of a device onto which a bilirubin solution was added dropwise.

A device was produced using the above-described UnaG (CΔ0)-NLuc (NΔ1) fusion protein, and bilirubin in a sample was measured using the device.
<Production Method of Device>
A device was produced using the following chemiluminescent indicator and chemiluminescent substrate.
Chemiluminescent indicator: 67.6 μM UnaG (CΔ0)-NLuc (NΔ1) fusion protein
Chemiluminescent substrate: 150 nM Coelenterazine-h
Using a 1,536 multi-well pattern function of a Certus liquid dispenser (manufactured by Gyger), 30 nL droplets of each of the chemiluminescent indicator and the chemiluminescent substrate were patterned on a cover glass or a Parafilm so as to form a checkered pattern as shown in FIG. 1A. The distance between the droplets (diameter: 1 to 2 mm) (the distance between the centers of adjacent droplets) was set to 2 mm.
<Measurement of Bilirubin>
5 μL of 100 nM bilirubin solution or 5 μL of phosphate buffer solution (PBS) (without bilirubin) was added dropwise on the device in a darkroom, and an image of a chemiluminescent signal was taken with a color camera (α7, manufactured by Sony Corporation) with ISO set to 25,600 and an exposure time set to 0.5 seconds. Furthermore, an image of the chemiluminescent signal was taken with a camera of a smartphone (iPhone® 6, manufactured by Apple Inc.) with ISO set to 1,500 and an exposure time set to 0.5 seconds. The results thereof are shown in FIGS. 7A and 7B.
FIG. 7A is the chemiluminescence image taken with the color camera, and FIG. 7B is the chemiluminescence image taken with the camera of the smartphone. As can be seen in FIGS. 7A and 7B, a portion where the droplet of the bilirubin solution was placed and a portion where the droplet of the phosphate buffer (without bilirubin) was placed exhibited different luminescent colors. Moreover, the luminescence data (luminescent colors) thereof exhibited a tendency similar to that shown in FIG. 6.
From these result, it was found that, on the basis of the correlation data as shown in FIG. 6, the concentration of bilirubin in solutions can be calculated from luminescence data (luminescent color) obtained using the device of the present disclosure.

Example 2

Figure 8A:
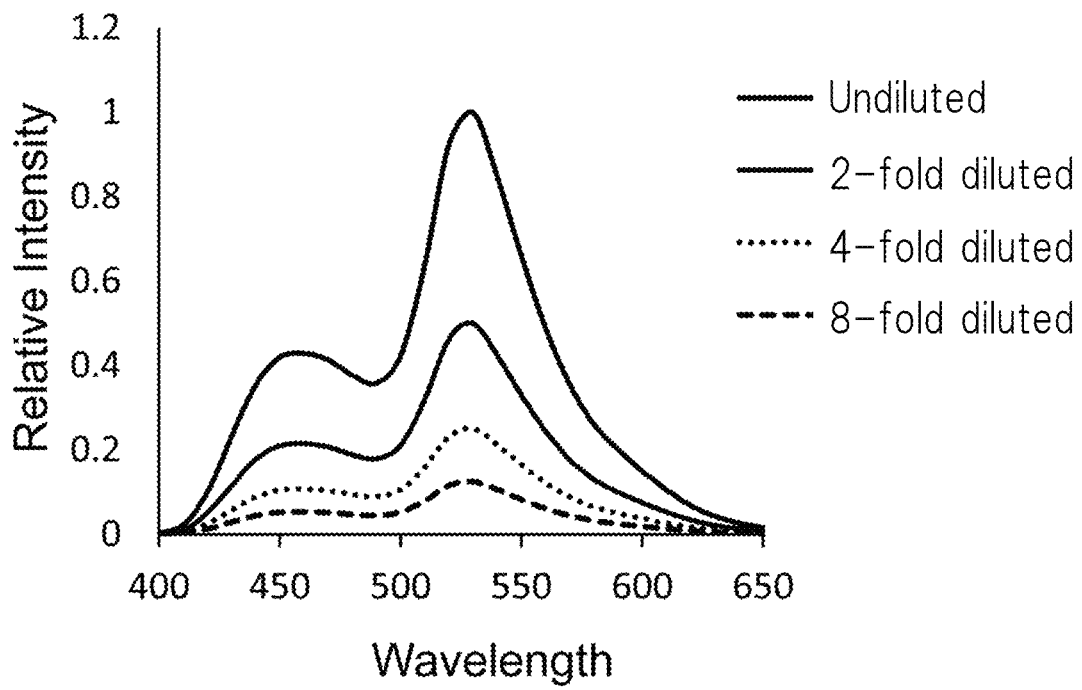
FIGS. 8A and 8B show an example of the result of bilirubin measurement using a UnaG (CΔ0)-NLuc (NΔ1) fusion protein in Example 2.
Figure 8B:
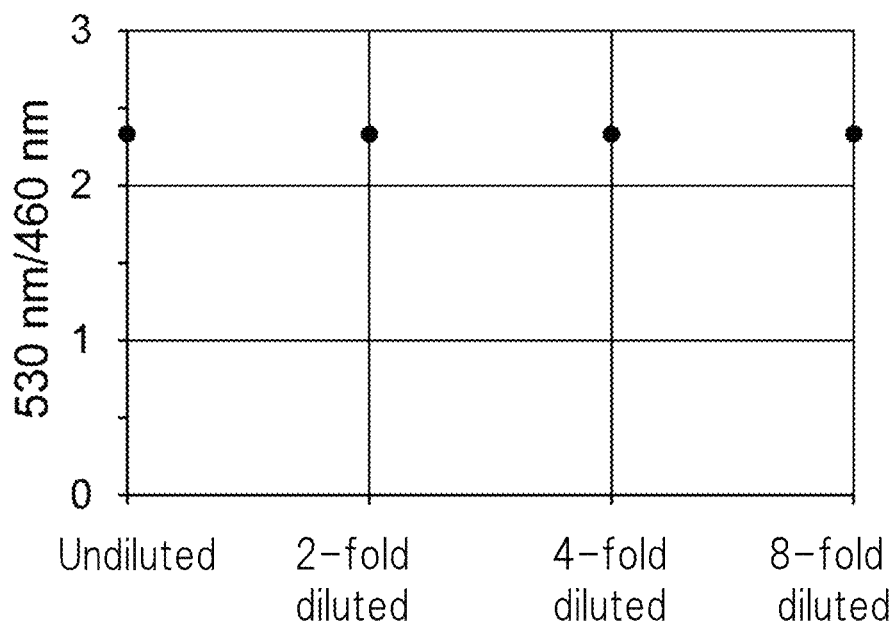

Undiluted, 2-fold diluted, 4-fold diluted, or 8-fold diluted UnaG (CΔ0)-NLuc (NΔ1) fusion protein solution was mixed with bilirubin-luminescent substrate (Coelenterazine-h) solution at a predetermined concentration. Luminescence spectra were measured using a multichannel spectrometer (PMA-12, manufactured by Hamamatsu Photonics K.K.), and from the obtained luminescence intensities, the ratio value (530 nm/460 nm) of the luminescence intensity at a luminescence wavelength of UnaG (530 nm) to the luminescence intensity at the luminescence wavelength of NLuc (460 nm) was calculated. FIGS. 8A and 8B show an example of the result obtained. In FIGS. 8A and 8B, FIG. 8A shows chemiluminescence spectra, and FIG. 8B is a graph showing the relationship between the dilution ratio of the UnaG (CΔ0)-NLuc (NΔ1) fusion protein solution (detection reagent) and the ratio value (530 nm/460 nm).

Comparative Example 1

Figure 9A:
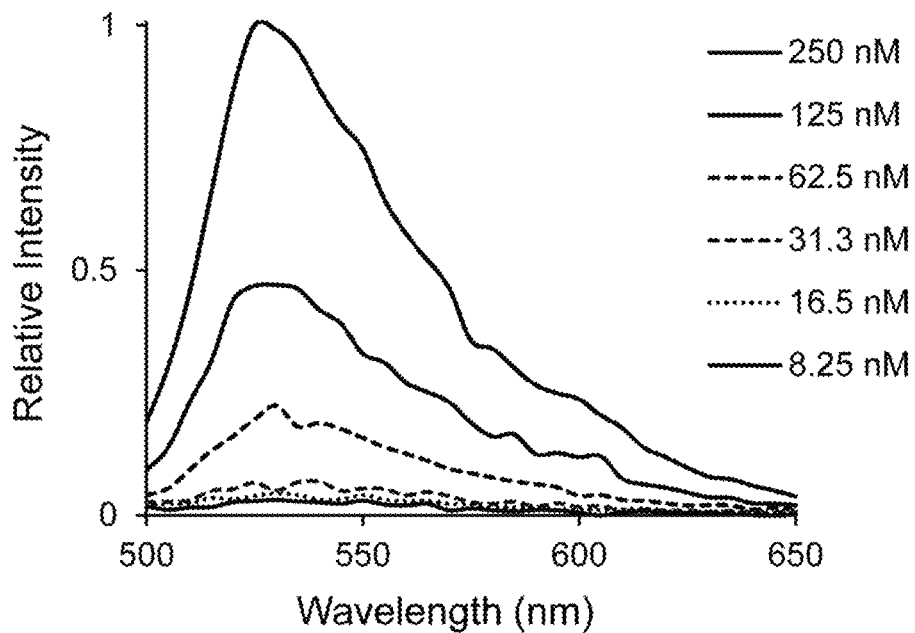
FIGS. 9A and 9B show an example of the result of bilirubin measurement using a UnaG protein in Comparative Example 1.
Figure 9B:
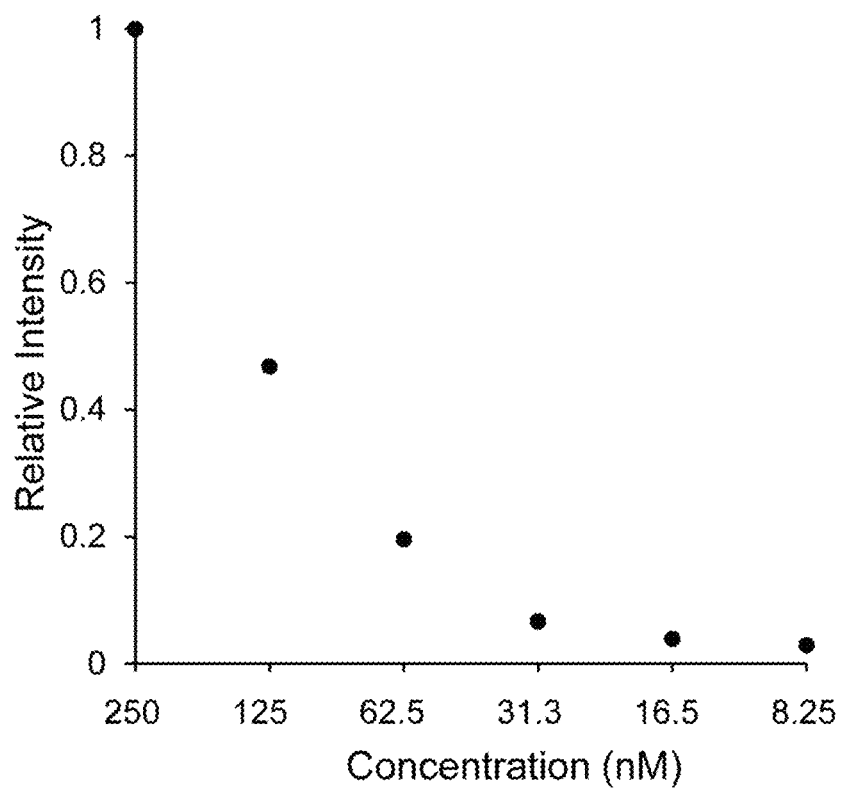

To each well of a 96-well plate (black), 50 μL of UnaG protein solution (8.25 nM, 16.5 nM, 31.5 nM, 62.5 nM, 125 nM, or 250 nM) was added, and then, 50 μL of 400 nM bilirubin solution was added. The 96-well plate was irradiated with excitation light having a wavelength of 450 nm using a microplate reader (SH-9000, manufactured by Corona), and thereafter, fluorescence spectra were obtained FIGS. 9A and 9B show an example of the result obtained. In FIGS. 9A and 9B, FIG. 9A shows fluorescence spectra, and FIG. 9B is a graph showing the relationship between the concentration of the UnaG protein solution (detection reagent) and the fluorescence intensity at the luminescence wavelength (530 nm) of UnaG.
In Comparative Example 1, as shown in FIGS. 9A and 9B, the fluorescence intensity changed depending on the concentration of the detection reagent in spite of the fact that the concentration of bilirubin to be detected was the same. That is to say, in Comparative Example 1 (a method using a UnaG protein), quantitative measurement cannot be performed.
In contrast, in Example 2 in which the measurement was performed using the UnaG (CΔ0)-NLuc (NΔ1) fusion protein, the waveforms of the spectra were uniform (FIG. 8A) while the luminescence intensity varied depending on the concentration of the detection reagent, and also, as can be seen in FIG. 8B, the peak ratio values (530 nm/460 nm) calculated for the same bilirubin concentrations were substantially the same regardless of the concentration of the detection reagent. Accordingly, it can be said that the UnaG (CΔ0)-NLuc (NΔ1) fusion protein enables measurement that is not affected by the concentration of the detection reagent, i.e., quantitative measurement.

[Sequence Listing Free Text]

SEQ ID NO: 1: Forward primer

SEQ ID NO: 2: Reverse primer

SEQ ID NO: 3: Reverse primer

SEQ ID NO: 4: Reverse primer

SEQ ID NO: 5: Reverse primer

SEQ ID NO: 6: Reverse primer

SEQ ID NO: 7: Forward primer

SEQ ID NO: 8: Forward primer

SEQ ID NO: 9: Forward primer

SEQ ID NO: 10: Reverse primer

SEQ ID NO: 11: Base sequence of UnaG (C 0)-NLuc (N 1) fusion protein

SEQ ID NO: 12: Amino acid sequence of UnaG (C 0)-NLuc (N 1) fusion protein

SEQ ID NO: 13: Forward primer

SEQ ID NO: 14: Reverse primer

SEQ ID NO: 15: Forward primer

SEQ ID NO: 16: Forward primer

SEQ ID NO: 17: Forward primer

SEQ ID NO: 18: Reverse primer

The invention claimed is:

1. A device comprising:
   a reagent portion in which a chemiluminescent indicator and a chemiluminescent substrate for the indicator are disposed; and
   a base on which the reagent portion is formed,
   wherein the chemiluminescent indicator and the chemiluminescent substrate are disposed independently from each other in the reagent portion, and in such a manner that the chemiluminescent indicator and the chemiluminescent substrate can react with each other when the sample is supplied to the reagent portion,
   wherein the chemiluminescent indicator is a fusion protein (C) in which a protein (A) capable of binding an analyte in a sample and a chemiluminescent protein (B) are fused together,
   the protein (A) and the protein (B) are linked so that resonance energy transfer can occur,
   the protein (A) is a protein (A1) that can emit fluorescence in a state where the analyte is bound thereto,
   the protein (B) can excite fluorescence or autofluorescence of the protein (A) with its luminescence energy, and
   the chemiluminescent substrate is a substrate for the protein (B).

2. The device according to claim 1, wherein the chemiluminescent indicator and the chemiluminescent substrate are disposed in dry state on the base.

3. The device according to claim 2, wherein the chemiluminescent indicator and the chemiluminescent substrate are disposed alternately so as to form a mosaic pattern.

4. The device according to claim 1, wherein the material of the base is a material selected from the group consisting of paraffin, a fluorine-based material, glass, polypropylene, woven fabric, non-woven fabric, and paper.

5. The device according to claim 1, wherein the protein (A1) is a UnaG protein or a variant thereof, each of which can emit fluorescence in a state where bilirubin is bound thereto, and the analyte to be detected is bilirubin.

6. The device according to claim 1, wherein the protein (A1) is a protein selected from the group consisting of IFP (infrared-fluorescent protein), and smURFP (small ultra-red fluorescent protein), each of which can emit fluorescence in a state where biliverdin is bound thereto, and the analyte to be detected is biliverdin.

7. The device according to claim 1, wherein the protein (B) is a protein selected from the group consisting of luciferase, aequorin, bacterial luciferase, and variants thereof.

8. The device according to claim 1, wherein the protein (B) is NLuc (NanoLuc Luciferase).

9. A device comprising:
   a reagent portion in which a chemiluminescent indicator and a chemiluminescent substrate for the indicator are disposed; and
   a base on which the reagent portion is formed,
   wherein the chemiluminescent indicator and the chemiluminescent substrate are disposed independently from each other in the reagent portion, and in such a manner that the chemiluminescent indicator and the chemiluminescent substrate can react with each other when the sample is supplied to the reagent portion,
   wherein the chemiluminescent indicator is a fusion protein (C) in which a protein (A) capable of binding an analyte in the sample and a chemiluminescent protein (B) are fused together,
   the protein (A) and the protein (B) are linked so that resonance energy transfer can occur,
   the protein (A) is a protein (A2) that can emit fluorescence on binding an autofluorescent molecule,
   the protein (B) can excite fluorescence or autofluorescence of the protein (A) with its luminescence energy, and
   the chemiluminescent substrate is a substrate for the protein (B).

10. The method according to claim 9, wherein the protein (A2) is a protein selected from the group consisting of FbFP (flavin mononucleotide (FMN)-based fluorescent protein), iLOV (improved light, oxygen, voltage) proteins, mini-SOG (mini singlet oxygen generator) proteins or a variant thereof, each capable of binding flavin mononucleotide, and the analyte to be detected is flavin mononucleotide.

11. The device according to claim 9, wherein the protein (B) is a protein selected from the group consisting of luciferase, aequorin, bacterial luciferase, and variants thereof.

12. The device according to claim 9, wherein the chemiluminescent indicator and the chemiluminescent substrate are disposed in dry state on the base.

13. The device according to claim 9, wherein the chemiluminescent indicator and the chemiluminescent substrate are disposed alternately so as to form a mosaic pattern.

14. The device according to claim 9, wherein the material of the base is a material selected from the group consisting of paraffin, a fluorine-based material, glass, polypropylene, woven fabric, non-woven fabric, and paper.

* * * * *

SEQUENCE LISTING

<160> NUMBER OF SEQ ID NOS: 18

<210> SEQ ID NO 1
<211> LENGTH: 26
<212> TYPE: DNA
<213> ORGANISM: Artificial Sequence
<220> FEATURE:
<223> OTHER INFORMATION: Forward primer

<400> SEQUENCE: 1
cgcggatccg ggtggttctg gtatgg                                              26

<210> SEQ ID NO 2
<211> LENGTH: 24
<212> TYPE: DNA
<213> ORGANISM: Artificial Sequence
<220> FEATURE:
<223> OTHER INFORMATION: Reverse primer0

<400> SEQUENCE: 2
gctggtacct tccgtcgccc tccg                                                24

<210> SEQ ID NO 3
<211> LENGTH: 24
<212> TYPE: DNA
<213> ORGANISM: Artificial Sequence
<220> FEATURE:
<223> OTHER INFORMATION: Reverse primer1

<400> SEQUENCE: 3
gctggtaccc gtcgccctcc ggta                                                24

<210> SEQ ID NO 4
<211> LENGTH: 24
<212> TYPE: DNA
<213> ORGANISM: Artificial Sequence
<220> FEATURE:
<223> OTHER INFORMATION: Reverse primer2

<400> SEQUENCE: 4
gctggtaccc gccctccggt agct                                                24

<210> SEQ ID NO 5
<211> LENGTH: 24
<212> TYPE: DNA
<213> ORGANISM: Artificial Sequence
<220> FEATURE:
<223> OTHER INFORMATION: Reverse primer3

<400> SEQUENCE: 5
gctggtaccc ctccggtagc tgcg                                                24

<210> SEQ ID NO 6
<211> LENGTH: 24
<212> TYPE: DNA
<213> ORGANISM: Artificial Sequence
<220> FEATURE:
<223> OTHER INFORMATION: Reverse primer4

<400> SEQUENCE: 6
gctggtaccc cggtagctgc gcac                                                24

<210> SEQ ID NO 7
<211> LENGTH: 31
<212> TYPE: DNA
<213> ORGANISM: Artificial Sequence

```
<220> FEATURE:
<223> OTHER INFORMATION: Forward primer 1

<400> SEQUENCE: 7
gccggtaccg tcttcacact cgaagatttc g                              31

<210> SEQ ID NO 8
<211> LENGTH: 30
<212> TYPE: DNA
<213> ORGANISM: Artificial Sequence
<220> FEATURE:
<223> OTHER INFORMATION: Forward primer 2

<400> SEQUENCE: 8
gccggtaccc tcgaagattt cgttggggac                                30

<210> SEQ ID NO 9
<211> LENGTH: 31
<212> TYPE: DNA
<213> ORGANISM: Artificial Sequence
<220> FEATURE:
<223> OTHER INFORMATION: Forward primer 3

<400> SEQUENCE: 9
gccggtaccg aagatttcgt tggggactgg c                              31

<210> SEQ ID NO 10
<211> LENGTH: 32
<212> TYPE: DNA
<213> ORGANISM: Artificial Sequence
<220> FEATURE:
<223> OTHER INFORMATION: Reverse primer

<400> SEQUENCE: 10
atgaattctt acgccagaat gcgttcgcac ag                             32

<210> SEQ ID NO 11
<211> LENGTH: 948
<212> TYPE: DNA
<213> ORGANISM: Artificial Sequence
<220> FEATURE:
<223> OTHER INFORMATION: UnaG(C 0)-NLuc(N 1)

<400> SEQUENCE: 11
ggtggttctg gtatggtcga gaaatttgtt ggcacctgga gatcgcaga cagccataat    60 tttggtgaat acctgaaagc tatcggagcc ccaaaggaat taagcgatgg tggggatgcc   120
acgacgccga cattgtacat ctcccagaag gacggagaca aaatgacagt gaaaatagag   180
aatggacctc ctacgttcct tgacactcaa gtaaagttca attaggggga ggagttcgac   240
gaatttcctt ctgatcgaag aaaaggcgta aaatctgtcg tgaacttggt gggagagaag   300
ctggtgtacg tacaaaagtg ggacggcaag gagacgacgt atgtccgaga gataaaggac   360
ggtaaactgg tcgtgacact tacgatggga cgtcgtggg ctgtgcgcag ctaccggagg     420
gcgacggaag gtaccgtctt cacactcgaa gatttcgttg ggactggcg acagacagcc    480 ggctacaacc tggaccaagt ccttgaacag ggaggtgtgt ccagtttgtt tcagaatctc   540
ggggtgtccg taactccgat ccaaaggatt gtcctgagcg tgaaaatgg ctgaagatc     600 gacatccatg tcatcatccc gtatgaaggt ctgagcggcg accaaatggg ccagatcgaa   660 aaaatttta agtggtgta ccctgtggat gatcatcact ttaaggtgat cctgcactat     720
ggcacactgg taatcgacgg ggttacgccg aacatgatcg actatttcgg acggccgtat   780
```

```
gaaggcatcg ccgtgttcga cggcaaaaag atcactgtaa cagggaccct gtggaacggc      840
aacaaaatta tcgacgagcg cctgatcaac cccgacggct ccctgctgtt ccgagtaacc      900
atcaacggag tgaccggctg gcggctgtgc gaacgcattc tggcgtaa                  948
```

```
<210> SEQ ID NO 12
<211> LENGTH: 313
<212> TYPE: PRT
<213> ORGANISM: Artificial Sequence
<220> FEATURE:
<223> OTHER INFORMATION: UnaG(C 0)-NLuc(N 1)

<400> SEQUENCE: 12
```

| | | | | | | | | | | | | | | |
|---|---|---|---|---|---|---|---|---|---|---|---|---|---|---|
| Gly | Gly | Ser | Gly | Met | Val | Glu | Lys | Phe | Val | Gly | Thr | Trp | Lys | Ile | Ala |
| 1 | | | | 5 | | | | | 10 | | | | | 15 | |
| Asp | Ser | His | Asn | Phe | Gly | Glu | Tyr | Leu | Lys | Ala | Ile | Gly | Ala | Pro | Lys |
| | | | 20 | | | | | 25 | | | | | 30 | | |
| Glu | Leu | Ser | Asp | Gly | Gly | Asp | Ala | Thr | Thr | Pro | Thr | Leu | Tyr | Ile | Ser |
| | | 35 | | | | | 40 | | | | | 45 | | | |
| Gln | Lys | Asp | Gly | Asp | Lys | Met | Thr | Val | Lys | Ile | Glu | Asn | Gly | Pro | Pro |
| | 50 | | | | | 55 | | | | | 60 | | | | |
| Thr | Phe | Leu | Asp | Thr | Gln | Val | Lys | Phe | Lys | Leu | Gly | Glu | Glu | Phe | Asp |
| 65 | | | | | 70 | | | | | 75 | | | | | 80 |
| Glu | Phe | Pro | Ser | Asp | Arg | Arg | Lys | Gly | Val | Lys | Ser | Val | Val | Asn | Leu |
| | | | | 85 | | | | | 90 | | | | | 95 | |
| Val | Gly | Glu | Lys | Tyr | Val | Gln | Lys | Trp | Asp | Gly | Lys | Glu | Thr | Thr | Tyr |
| | | | 100 | | | | | 105 | | | | | 110 | | |
| Val | Arg | Glu | Ile | Lys | Asp | Gly | Lys | Leu | Val | Val | Thr | Leu | Thr | Met | Gly |
| | | 115 | | | | | 120 | | | | | 125 | | | |
| Asp | Val | Val | Ala | Val | Arg | Ser | Tyr | Arg | Arg | Ala | Thr | Glu | Gly | Thr | Val |
| | 130 | | | | | 135 | | | | | 140 | | | | |
| Phe | Thr | Leu | Glu | Asp | Phe | Val | Gly | Asp | Trp | Arg | Gln | Thr | Ala | Gly | Tyr |
| 145 | | | | | 150 | | | | | 155 | | | | | 160 |
| Asn | Leu | Asp | Gln | Val | Leu | Glu | Gln | Gly | Gly | Val | Ser | Ser | Leu | Phe | Gln |
| | | | | 165 | | | | | 170 | | | | | 175 | |
| Asn | Leu | Gly | Val | Ser | Val | Thr | Pro | Ile | Gln | Arg | Ile | Val | Leu | Ser | Gly |
| | | | 180 | | | | | 185 | | | | | 190 | | |
| Glu | Asn | Gly | Leu | Lys | Ile | Asp | Ile | His | Val | Ile | Ile | Pro | Tyr | Glu | Gly |
| | | 195 | | | | | 200 | | | | | 205 | | | |
| Leu | Ser | Gly | Asp | Gln | Met | Gly | Gln | Ile | Glu | Lys | Ile | Phe | Lys | Val | Val |
| | 210 | | | | | 215 | | | | | 220 | | | | |
| Tyr | Pro | Val | Asp | Asp | His | His | Phe | Lys | Val | Ile | Leu | His | Tyr | Gly | Thr |
| 225 | | | | | 230 | | | | | 235 | | | | | 240 |
| Leu | Val | Ile | Asp | Gly | Val | Thr | Pro | Asn | Met | Ile | Asp | Tyr | Phe | Gly | Arg |
| | | | | 245 | | | | | 250 | | | | | 255 | |
| Pro | Tyr | Glu | Gly | Ile | Ala | Val | Phe | Asp | Gly | Lys | Lys | Ile | Thr | Val | Thr |
| | | | 260 | | | | | 265 | | | | | 270 | | |
| Gly | Thr | Leu | Trp | Asn | Gly | Asn | Lys | Ile | Ile | Asp | Glu | Arg | Leu | Ile | Asn |
| | | 275 | | | | | 280 | | | | | 285 | | | |
| Pro | Asp | Gly | Ser | Leu | Leu | Phe | Arg | Val | Thr | Ile | Asn | Gly | Val | Thr | Gly |
| | 290 | | | | | 295 | | | | | 300 | | | | |
| Trp | Arg | Leu | Cys | Glu | Arg | Ile | Leu | Ala | | | | | | | |
| 305 | | | | | 310 | | | | | | | | | | |

```
<210> SEQ ID NO 13
<211> LENGTH: 27
```

```
<212> TYPE: DNA
<213> ORGANISM: Artificial Sequence
<220> FEATURE:
<223> OTHER INFORMATION: Forward primer
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (3)..(3)
<223> OTHER INFORMATION: k is g, or t
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (6)..(6)
<223> OTHER INFORMATION: k is g, or t

<400> SEQUENCE: 13
nnknnkgtct tcacactcga agatttc                                          27

<210> SEQ ID NO 14
<211> LENGTH: 22
<212> TYPE: DNA
<213> ORGANISM: Artificial Sequence
<220> FEATURE:
<223> OTHER INFORMATION: Reverse primer

<400> SEQUENCE: 14
ttccgtcgcc ctccggtagc tg                                               22

<210> SEQ ID NO 15
<211> LENGTH: 24
<212> TYPE: DNA
<213> ORGANISM: Artificial Sequence
<220> FEATURE:
<223> OTHER INFORMATION: Forward primer

<400> SEQUENCE: 15
ggcgtcttca cactcgaaga tttc                                             24

<210> SEQ ID NO 16
<211> LENGTH: 27
<212> TYPE: DNA
<213> ORGANISM: Artificial Sequence
<220> FEATURE:
<223> OTHER INFORMATION: Forward primer

<400> SEQUENCE: 16
ggcggcgtct tcacactcga agatttc                                          27

<210> SEQ ID NO 17
<211> LENGTH: 30
<212> TYPE: DNA
<213> ORGANISM: Artificial Sequence
<220> FEATURE:
<223> OTHER INFORMATION: Forward primer

<400> SEQUENCE: 17
ggcggcagcg tcttcacact cgaagatttc                                       30

<210> SEQ ID NO 18
<211> LENGTH: 19
<212> TYPE: DNA
<213> ORGANISM: Artificial Sequence
<220> FEATURE:
```

-continued

```
<223> OTHER INFORMATION: Reverse primer

<400> SEQUENCE: 18
ggtaccttcc gtcgccctc                                               19
```